(12) United States Patent
Nam et al.

(10) Patent No.: US 11,046,742 B2
(45) Date of Patent: Jun. 29, 2021

(54) FUSION PROTEIN COMPRISING CCL3 VARIANT AND USE THEREOF

(71) Applicant: YUHAN CORPORATION, Seoul (KR)

(72) Inventors: Su Youn Nam, Seoul (KR); Jong Gyun Kim, Gyeonggi-do (KR); Byung Hyun Choi, Gyeonggi-do (KR); June Hyung Lee, Seoul (KR); Ju Young Park, Gyeonggi-do (KR); Jun Kyung Lee, Gyeonggi-do (KR); Na Rae Lee, Seoul (KR); Ki Hong Kim, Gyeonggi-do (KR); Seul Gi Kim, Gyeonggi-do (KR); Se Woong Oh, Gyeonggi-do (KR); Seung Yub Shin, Gyeonggi-do (KR); Ho Woong Kang, Gyeonggi-do (KR); Su Jin Ahn, Gyeonggi-do (KR); Soo Yong Chung, Gyeonggi-do (KR)

(73) Assignee: YUHAN CORPORATION, Seoul (KR)

(*) Notice: Subject to any disclaimer, the term of this patent is extended or adjusted under 35 U.S.C. 154(b) by 0 days.

(21) Appl. No.: 16/097,572

(22) PCT Filed: Apr. 19, 2017

(86) PCT No.: PCT/KR2017/004199
§ 371 (c)(1),
(2) Date: Oct. 29, 2018

(87) PCT Pub. No.: WO2017/188653
PCT Pub. Date: Nov. 2, 2017

(65) Prior Publication Data
US 2019/0153055 A1 May 23, 2019

(30) Foreign Application Priority Data
Apr. 29, 2016 (KR) .................. 10-2016-0053018

(51) Int. Cl.
| | |
|---|---|
| C07K 14/52 | (2006.01) |
| C07K 19/00 | (2006.01) |
| C12N 15/09 | (2006.01) |
| C12N 15/11 | (2006.01) |
| C12N 15/63 | (2006.01) |
| A61K 38/19 | (2006.01) |
| A61K 47/68 | (2017.01) |
| A61P 35/00 | (2006.01) |
| A61K 38/00 | (2006.01) |
| A61K 47/50 | (2017.01) |

(52) U.S. Cl.
CPC .......... C07K 14/523 (2013.01); A61K 38/195 (2013.01); A61K 47/68 (2017.08); A61P 35/00 (2018.01); C07K 19/00 (2013.01); C12N 15/09 (2013.01); C12N 15/11 (2013.01); C12N 15/63 (2013.01); A61K 38/00 (2013.01); A61K 47/50 (2017.08); C07K 2319/30 (2013.01)

(58) Field of Classification Search
CPC ..... C07K 14/523; C07K 19/00; A61K 38/195
See application file for complete search history.

(56) References Cited

U.S. PATENT DOCUMENTS

| 5,856,301 A * | 1/1999 | Craig .................. | C12N 15/815 514/21.2 |
|---|---|---|---|
| 6,730,296 B1 | 5/2004 | Herrmann et al. | |
| 7,638,319 B2 | 12/2009 | Cardozo et al. | |
| 8,445,442 B2 | 5/2013 | Bosenberg et al. | |
| 2008/0300188 A1* | 12/2008 | Yang .................... | C12N 15/62 514/7.6 |
| 2013/0171140 A1 | 7/2013 | Ruffini et al. | |
| 2016/0115216 A1 | 4/2016 | Hubalek et al. | |

FOREIGN PATENT DOCUMENTS

| JP | 7-502404 A | 3/1995 |
|---|---|---|
| JP | 2005522192 A | 7/2005 |
| JP | 2005525089 A | 8/2005 |
| JP | 2006514699 A | 5/2006 |
| JP | 2007502404 A | 2/2007 |
| JP | 2007528194 A | 10/2007 |
| JP | 2007537148 A | 12/2007 |
| JP | 2009504158 A | 2/2009 |
| JP | 2014518632 A | 8/2014 |
| JP | 2014522644 A | 9/2014 |
| RU | 2530168 C2 | 10/2014 |
| WO | WO9838212 A2 | 9/1998 |

(Continued)

OTHER PUBLICATIONS

Mueller et al (2006. Biochemical Pharmcology. 72: 739-748).*

(Continued)

Primary Examiner — Zachary C Howard
(74) Attorney, Agent, or Firm — Hultquist, PLLC; Steven J. Hultquist

(57) ABSTRACT

Provided are a fusion protein having a CCL3 variant with improved in vivo persistency, protein stability and pharmacological activity and a use thereof, more particularly, a fusion protein comprising a CCL3 variant and an immunoglobulin Fc region and a use thereof as a therapeutic agent for lymphopenia, cancer or infection, in which an N-terminal amino acid of a wild-type CCL3α or CCL3β is deleted and an amino acid at a specific position is substituted with a different amino acid at the same position of the wild-type CCL3α or CCL3β in the CCL3 variant.

8 Claims, 3 Drawing Sheets
Specification includes a Sequence Listing.

(56) References Cited

FOREIGN PATENT DOCUMENTS

| WO | WO2007113285 A2 | 10/2007 |
|---|---|---|
| WO | WO2012023631 A1 | 2/2012 |

OTHER PUBLICATIONS

Colobran et al (2010. Clinical and Experimental Immunology. 162: 41-52).*

Struyf et al (2001. Eur J Immunol. 31: 2170-2178).*

Bachmann, M., et al., "Chemokines: More Than Just Road Signs", "Nature Reviews—Immunology", Feb. 2006, pp. 159-164, vol. 6.

Cittera, E., et al., "The CCL3 Family of Chemokines and Innate Immunity Cooperate In Vivo in the Eradication of an Established Lymphoma Xenograft by Rituximab", "The Journal of Immunology", 2007, pp. 6613-6623, vol. 178.

Gilmore, G., et al., "Protective Effects of BB-10010 Treatment on Chemotherapy-Induced Neutropenia in Mice", "Experimental Hematology", 1999, pp. 195-202, vol. 27.

Kufareva, I., et al., "Chemokine and Chemokine Receptor Structure and Interactions: Implications for Therapeutic Strategies", "Immunology and Cell Biology", 2015, pp. 372-383, vol. 93.

Marshall, E., et al., "Clinical Effects of Human Macrophage Inflammatory Protein-1 Alpha MIP-1 alpha (LD78) Administration to Humans: a Phase I Study in Cancer Patients and Normal Healthy Volunteers with the Genetic Engineered Variant, BB-10010", "European Journal of Cancer", 1998, pp. 1023 1029, vol. 34, No. 7.

Menten, P., et al., "Macrophage Inflammatory Protein-1", "Cytokine & Growth Factor Reviews", 2002, pp. 455-481, vol. 13.

Ren, M., et al., "Polymerization of MIP-1 Chemokine (CCL3 and CCL4) and Clearance of MIP-1 by Insulin-Degrading Enzyme", "The EMBO Journal", 2010, pp. 3952-3966, vol. 29.

Shiraishi, K., et al., "Enhancement of Antitumor Radiation Efficacy and Consistent Induction of the Abscopal Effect in Mice by EC1301, an Active Variant of Macrophage Inflammatory Protein-1 alpha", "Clinical Cancer Research", Feb. 15, 2008, pp. 1159-1166, vol. 14, No. 4.

Czaplewski, L.G., et al., "Identification of Amino Acid Residues Critical for Aggregation of Human CC Chemokine Macrophage Inflammatory Protein (MIP)-1alpha, MIP-1beta, and RANTES", "The Journal of Biological Chemistry", 1999, pp. 16077-16084, vol. 274, No. 23.

Hunter, M.G., et al., "BB-10010: An Active Variant of Human Macrophage Inflammatory Protein-1 alpha With Improved Pharmaceutical Properties", "TheBlood, American Society of Hematology", 1995, pp. 4400-4408, vol. 86, No. 12.

Mueller, A., et al., "Diverse Signalling by Different Chemokines Through the Chemokine Receptor CCR5", "Biochemical Pharmacology", 2006, pp. 739-748, vol. 72, No. 6.

Chen, X., et al., "Fusion Protein Linkers: Property, Design and Functionality", "Advanced Drug Delivery Reviews", 2013, pp. 1357-1369, vol. 65.

Maeda, Y., et al., "Engineering of Functional Chimeric Protein G—Vargula Luciferase", "Analytical Biochemistry", 1997, pp. 147-152, vol. 249, No. Article AB972181.

Saunders, K.O., "Conceptual Approaches to Modulating Antibody Effector Functions and Circulation Half-Life", "Frontiers in Immunology", Jun. 2019, pp. 1-20, vol. 10, No. Article 1296.

Suzuki, T., et al., "Importance of Neonatal FcR in Regulating the Serum Half-Life of Therapeutic Proteins Containing the Fc Domain of Human IgG1: A Comparative Study of the Affinity of Monoclonal Antibodies and Fc-Fusion Proteins to Human Neotal FcR", "J. Immunol.", Jan. 18, 2010, pp. 1968-1976, vol. 184.

Wu, B., et al., "Pharmacokinetics of Peptide-Fc Fusion Proteins", "Journal of Pharmaceutical Sciences", 2014, pp. 53-64, vol. 103.

Allen, F., et al., "CCL3 Augments Tumor Rejection and Enhances CD8+ T Cell Infiltration Through NK and CD103 + Dendritic Cell Recruitment via IFN", "OncoImmunology", 2018, pp. e1393598-1-e1393598-11, vol. 7, No. 3.

"Anti-Tumor Efficacy of YH24931", "Supplemental Data for CRC (Colorectal Cancer)", 2018, p. 1.

Kanegasaki, S., et al., "Macrophage Inflammatory Protein Derivative ECI301 Enhances the Alarmin-Associated Abscopal Benefits of Tumor Radiotherapy", "Cancer Res", Sep. 15, 2014, pp. 5070-5079, vol. 74, No. 18.

Kang, T., et al., "The Effect of CCL3 to Anti-Tumor Responses", 2014, p. 1.

* cited by examiner

SEQUENCE LISTING

<160> NUMBER OF SEQ ID NOS: 17

<210> SEQ ID NO 1
<211> LENGTH: 70
<212> TYPE: PRT
<213> ORGANISM: Artificial Sequence
<220> FEATURE:
<223> OTHER INFORMATION: human CCL3 alpha

<400> SEQUENCE: 1

Ala Ser Leu Ala Ala Asp Thr Pro Thr Ala Cys Cys Phe Ser Tyr Thr
1               5                   10                  15

Ser Arg Gln Ile Pro Gln Asn Phe Ile Ala Asp Tyr Phe Glu Thr Ser
            20                  25                  30

Ser Gln Cys Ser Lys Pro Gly Val Ile Phe Leu Thr Lys Arg Ser Arg
        35                  40                  45

Gln Val Cys Ala Asp Pro Ser Glu Glu Trp Val Gln Lys Tyr Val Ser
    50                  55                  60

Asp Leu Glu Leu Ser Ala
65                  70

<210> SEQ ID NO 2
<211> LENGTH: 69
<212> TYPE: PRT
<213> ORGANISM: Artificial Sequence
<220> FEATURE:
<223> OTHER INFORMATION: CCL3 alpha variant

<400> SEQUENCE: 2

Ser Leu Ala Ala Asp Thr Pro Thr Ala Cys Cys Phe Ser Tyr Thr Ser
1               5                   10                  15

Arg Gln Ile Pro Gln Asn Phe Ile Ala Ala Tyr Phe Glu Thr Ser Ser
            20                  25                  30

Gln Cys Ser Lys Pro Gly Val Ile Phe Leu Thr Lys Arg Ser Arg Gln
        35                  40                  45

Val Cys Ala Asp Pro Ser Glu Glu Trp Val Gln Lys Tyr Val Ser Asp
    50                  55                  60

Leu Glu Leu Ser Ala
65

<210> SEQ ID NO 3
<211> LENGTH: 70
<212> TYPE: PRT
<213> ORGANISM: Artificial Sequence
<220> FEATURE:
<223> OTHER INFORMATION: human CCL3 beta

<400> SEQUENCE: 3

Ala Pro Leu Ala Ala Asp Thr Pro Thr Ala Cys Cys Phe Ser Tyr Thr
1               5                   10                  15

Ser Arg Gln Ile Pro Gln Asn Phe Ile Ala Asp Tyr Phe Glu Thr Ser
            20                  25                  30

Ser Gln Cys Ser Lys Pro Ser Val Ile Phe Leu Thr Lys Arg Gly Arg
        35                  40                  45

Gln Val Cys Ala Asp Pro Ser Glu Glu Trp Val Gln Lys Tyr Val Ser
    50                  55                  60

Asp Leu Glu Leu Ser Ala
65                  70

<210> SEQ ID NO 4

```
<211> LENGTH: 68
<212> TYPE: PRT
<213> ORGANISM: Artificial Sequence
<220> FEATURE:
<223> OTHER INFORMATION: CCL3 beta variant

<400> SEQUENCE: 4

Leu Ala Ala Asp Thr Pro Thr Ala Cys Cys Phe Ser Tyr Thr Ser Arg
1               5                   10                  15

Gln Ile Pro Gln Asn Phe Ile Ala Ala Tyr Phe Glu Thr Ser Ser Gln
            20                  25                  30

Cys Ser Lys Pro Ser Val Ile Phe Leu Thr Lys Arg Gly Arg Gln Val
        35                  40                  45

Cys Ala Asp Pro Ser Glu Glu Trp Val Gln Lys Tyr Val Ser Asp Leu
    50                  55                  60

Glu Leu Ser Ala
65

<210> SEQ ID NO 5
<211> LENGTH: 12
<212> TYPE: PRT
<213> ORGANISM: Artificial Sequence
<220> FEATURE:
<223> OTHER INFORMATION: Linker

<400> SEQUENCE: 5

Arg Asn Thr Gly Arg Gly Gly Glu Glu Lys Lys Lys
1               5                   10

<210> SEQ ID NO 6
<211> LENGTH: 17
<212> TYPE: PRT
<213> ORGANISM: Artificial Sequence
<220> FEATURE:
<223> OTHER INFORMATION: Linker

<400> SEQUENCE: 6

Arg Asn Thr Gly Arg Gly Gly Glu Glu Lys Lys Lys Glu Glu Lys Lys
1               5                   10                  15

Lys

<210> SEQ ID NO 7
<211> LENGTH: 22
<212> TYPE: PRT
<213> ORGANISM: Artificial Sequence
<220> FEATURE:
<223> OTHER INFORMATION: Linker

<400> SEQUENCE: 7

Arg Asn Thr Gly Arg Gly Gly Glu Glu Lys Lys Lys Glu Glu Lys Lys
1               5                   10                  15

Lys Glu Glu Lys Lys Lys
            20

<210> SEQ ID NO 8
<211> LENGTH: 15
<212> TYPE: PRT
<213> ORGANISM: Artificial Sequence
<220> FEATURE:
<223> OTHER INFORMATION: Linker

<400> SEQUENCE: 8

Arg Asn Thr Arg Asn Thr Gly Arg Gly Gly Glu Glu Lys Lys Lys
1               5                   10                  15
```

<210> SEQ ID NO 9
<211> LENGTH: 20
<212> TYPE: PRT
<213> ORGANISM: Artificial Sequence
<220> FEATURE:
<223> OTHER INFORMATION: Linker

<400> SEQUENCE: 9

Arg Asn Thr Arg Asn Thr Gly Arg Gly Gly Glu Glu Lys Lys Lys Glu
1               5                   10                  15

Glu Lys Lys Lys
            20

<210> SEQ ID NO 10
<211> LENGTH: 25
<212> TYPE: PRT
<213> ORGANISM: Artificial Sequence
<220> FEATURE:
<223> OTHER INFORMATION: Linker

<400> SEQUENCE: 10

Arg Asn Thr Arg Asn Thr Gly Arg Gly Gly Glu Glu Lys Lys Lys Glu
1               5                   10                  15

Glu Lys Lys Lys Glu Glu Lys Lys Lys
            20                  25

<210> SEQ ID NO 11
<211> LENGTH: 18
<212> TYPE: PRT
<213> ORGANISM: Artificial Sequence
<220> FEATURE:
<223> OTHER INFORMATION: Linker

<400> SEQUENCE: 11

Arg Asn Thr Arg Asn Thr Arg Asn Thr Gly Arg Gly Gly Glu Glu Lys
1               5                   10                  15

Lys Lys

<210> SEQ ID NO 12
<211> LENGTH: 23
<212> TYPE: PRT
<213> ORGANISM: Artificial Sequence
<220> FEATURE:
<223> OTHER INFORMATION: Linker

<400> SEQUENCE: 12

Arg Asn Thr Arg Asn Thr Arg Asn Thr Gly Arg Gly Gly Glu Glu Lys
1               5                   10                  15

Lys Lys Glu Glu Lys Lys Lys
            20

<210> SEQ ID NO 13
<211> LENGTH: 28
<212> TYPE: PRT
<213> ORGANISM: Artificial Sequence
<220> FEATURE:
<223> OTHER INFORMATION: Linker

<400> SEQUENCE: 13

Arg Asn Thr Arg Asn Thr Arg Asn Thr Gly Arg Gly Gly Glu Glu Lys
1               5                   10                  15

Lys Lys Glu Glu Lys Lys Lys Glu Glu Lys Lys Lys
            20                  25

<210> SEQ ID NO 14
<211> LENGTH: 233
<212> TYPE: PRT
<213> ORGANISM: Artificial Sequence
<220> FEATURE:
<223> OTHER INFORMATION: HyFc

<400> SEQUENCE: 14

Glu Lys Glu Lys Glu Glu Gln Glu Glu Arg Glu Thr Lys Thr Pro Glu
1               5                   10                  15

Cys Pro Ser His Thr Gln Pro Leu Gly Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser Gln Glu Asp Pro Glu Val Gln Phe Asn Trp Tyr
    50                  55                  60

Val Asp Gly Val Glu Val His Asn Ala Lys Thr Lys Pro Arg Glu Glu
65                  70                  75                  80

Gln Phe Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Gly Leu Pro Ser Ser Ile Glu Lys Thr Ile Ser Lys Ala Lys Gly Gln
        115                 120                 125

Pro Arg Glu Pro Gln Val Tyr Thr Leu Pro Pro Ser Gln Glu Glu Met
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Arg Leu Thr Val Asp Lys Ser Arg Trp Gln Glu Gly Asn Val
        195                 200                 205

Phe Ser Cys Ser Val Met His Glu Ala Leu His Asn His Tyr Thr Gln
    210                 215                 220

Lys Ser Leu Ser Leu Ser Leu Gly Lys
225                 230

<210> SEQ ID NO 15
<211> LENGTH: 314
<212> TYPE: PRT
<213> ORGANISM: Artificial Sequence
<220> FEATURE:
<223> OTHER INFORMATION: CCL3A-H05

<400> SEQUENCE: 15

Ser Leu Ala Ala Asp Thr Pro Thr Ala Cys Cys Phe Ser Tyr Thr Ser
1               5                   10                  15

Arg Gln Ile Pro Gln Asn Phe Ile Ala Ala Tyr Phe Glu Thr Ser Ser
            20                  25                  30

Gln Cys Ser Lys Pro Gly Val Ile Phe Leu Thr Lys Arg Ser Arg Gln
        35                  40                  45

Val Cys Ala Asp Pro Ser Glu Glu Trp Val Gln Lys Tyr Val Ser Asp
    50                  55                  60

Leu Glu Leu Ser Ala Arg Asn Thr Gly Arg Gly Gly Glu Glu Lys Lys

```
                65                  70                  75                  80
Lys Glu Lys Glu Lys Glu Glu Gln Glu Arg Glu Thr Lys Thr Pro
                    85                  90                  95
Glu Cys Pro Ser His Thr Gln Pro Leu Gly Val Phe Leu Phe Pro
                100                 105                 110
Lys Pro Lys Asp Thr Leu Met Ile Ser Arg Thr Pro Glu Val Thr Cys
            115                 120                 125
Val Val Val Asp Val Ser Gln Glu Asp Pro Glu Val Gln Phe Asn Trp
        130                 135                 140
Tyr Val Asp Gly Val Glu Val His Asn Ala Lys Thr Lys Pro Arg Glu
145                 150                 155                 160
Glu Gln Phe Asn Ser Thr Tyr Arg Val Val Ser Val Leu Thr Val Leu
                165                 170                 175
His Gln Asp Trp Leu Asn Gly Lys Glu Tyr Lys Cys Lys Val Ser Asn
            180                 185                 190
Lys Gly Leu Pro Ser Ser Ile Glu Lys Thr Ile Ser Lys Ala Lys Gly
        195                 200                 205
Gln Pro Arg Glu Pro Gln Val Tyr Thr Leu Pro Pro Ser Gln Glu Glu
    210                 215                 220
Met Thr Lys Asn Gln Val Ser Leu Thr Cys Leu Val Lys Gly Phe Tyr
225                 230                 235                 240
Pro Ser Asp Ile Ala Val Glu Trp Glu Ser Asn Gly Gln Pro Glu Asn
                245                 250                 255
Asn Tyr Lys Thr Thr Pro Pro Val Leu Asp Ser Asp Gly Ser Phe Phe
            260                 265                 270
Leu Tyr Ser Arg Leu Thr Val Asp Lys Ser Arg Trp Gln Gln Gly Asn
        275                 280                 285
Val Phe Ser Cys Ser Val Met His Glu Ala Leu His Asn His Tyr Thr
    290                 295                 300
Gln Lys Ser Leu Ser Leu Ser Leu Gly Lys
305                 310

<210> SEQ ID NO 16
<211> LENGTH: 313
<212> TYPE: PRT
<213> ORGANISM: Artificial Sequence
<220> FEATURE:
<223> OTHER INFORMATION: CCL3B-H05

<400> SEQUENCE: 16

Leu Ala Ala Asp Thr Pro Thr Ala Cys Cys Phe Ser Tyr Thr Ser Arg
1               5                   10                  15
Gln Ile Pro Gln Asn Phe Ile Ala Ala Tyr Phe Glu Thr Ser Ser Gln
            20                  25                  30
Cys Ser Lys Pro Ser Val Ile Phe Leu Thr Lys Arg Gly Arg Gln Val
        35                  40                  45
Cys Ala Asp Pro Ser Glu Glu Trp Val Gln Lys Tyr Val Ser Asp Leu
    50                  55                  60
Glu Leu Ser Ala Arg Asn Thr Gly Arg Gly Gly Glu Lys Lys Lys
65                  70                  75                  80
Glu Lys Glu Lys Glu Glu Gln Glu Glu Arg Glu Thr Lys Thr Pro Glu
                85                  90                  95
Cys Pro Ser His Thr Gln Pro Leu Gly Val Phe Leu Phe Pro Pro Lys
            100                 105                 110
Pro Lys Asp Thr Leu Met Ile Ser Arg Thr Pro Glu Val Thr Cys Val
```

```
            115                 120                 125
Val Val Asp Val Ser Gln Glu Asp Pro Glu Val Gln Phe Asn Trp Tyr
130                 135                 140

Val Asp Gly Val Glu Val His Asn Ala Lys Thr Lys Pro Arg Glu Glu
145                 150                 155                 160

Gln Phe Asn Ser Thr Tyr Arg Val Val Ser Val Leu Thr Val Leu His
                165                 170                 175

Gln Asp Trp Leu Asn Gly Lys Glu Tyr Lys Cys Lys Val Ser Asn Lys
            180                 185                 190

Gly Leu Pro Ser Ser Ile Glu Lys Thr Ile Ser Lys Ala Lys Gly Gln
            195                 200                 205

Pro Arg Glu Pro Gln Val Tyr Thr Leu Pro Pro Ser Gln Glu Glu Met
210                 215                 220

Thr Lys Asn Gln Val Ser Leu Thr Cys Leu Val Lys Gly Phe Tyr Pro
225                 230                 235                 240

Ser Asp Ile Ala Val Glu Trp Glu Ser Asn Gly Gln Pro Glu Asn Asn
                245                 250                 255

Tyr Lys Thr Thr Pro Pro Val Leu Asp Ser Asp Gly Ser Phe Phe Leu
            260                 265                 270

Tyr Ser Arg Leu Thr Val Asp Lys Ser Arg Trp Gln Glu Gly Asn Val
            275                 280                 285

Phe Ser Cys Ser Val Met His Glu Ala Leu His Asn His Tyr Thr Gln
290                 295                 300

Lys Ser Leu Ser Leu Ser Leu Gly Lys
305                 310

<210> SEQ ID NO 17
<211> LENGTH: 301
<212> TYPE: PRT
<213> ORGANISM: Artificial Sequence
<220> FEATURE:
<223> OTHER INFORMATION: CCL3B-H40

<400> SEQUENCE: 17

Leu Ala Ala Asp Thr Pro Thr Ala Cys Cys Phe Ser Tyr Thr Ser Arg
1               5                   10                  15

Gln Ile Pro Gln Asn Phe Ile Ala Ala Tyr Phe Glu Thr Ser Ser Gln
                20                  25                  30

Cys Ser Lys Pro Ser Val Ile Phe Leu Thr Lys Arg Gly Arg Gln Val
            35                  40                  45

Cys Ala Asp Pro Ser Glu Glu Trp Val Gln Lys Tyr Val Ser Asp Leu
50                  55                  60

Glu Leu Ser Ala Glu Lys Glu Lys Glu Gln Glu Glu Arg Glu Thr
65                  70                  75                  80

Lys Thr Pro Glu Cys Pro Ser His Thr Gln Pro Leu Gly Val Phe Leu
                85                  90                  95

Phe Pro Pro Lys Pro Lys Asp Thr Leu Met Ile Ser Arg Thr Pro Glu
            100                 105                 110

Val Thr Cys Val Val Val Asp Val Ser Gln Glu Asp Pro Glu Val Gln
            115                 120                 125

Phe Asn Trp Tyr Val Asp Gly Val Glu Val His Asn Ala Lys Thr Lys
            130                 135                 140

Pro Arg Glu Glu Gln Phe Asn Ser Thr Tyr Arg Val Val Ser Val Leu
145                 150                 155                 160

Thr Val Leu His Gln Asp Trp Leu Asn Gly Lys Glu Tyr Lys Cys Lys
```

-continued

```
            165                 170                 175
Val Ser Asn Lys Gly Leu Pro Ser Ser Ile Glu Lys Thr Ile Ser Lys
            180                 185                 190

Ala Lys Gly Gln Pro Arg Glu Pro Gln Val Tyr Thr Leu Pro Pro Ser
            195                 200                 205

Gln Glu Glu Met Thr Lys Asn Gln Val Ser Leu Thr Cys Leu Val Lys
        210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Arg Leu Thr Val Asp Lys Ser Arg Trp Gln
            260                 265                 270

Glu Gly Asn Val Phe Ser Cys Ser Val Met His Glu Ala Leu His Asn
            275                 280                 285

His Tyr Thr Gln Lys Ser Leu Ser Leu Ser Leu Gly Lys
        290                 295                 300
```

FUSION PROTEIN COMPRISING CCL3 VARIANT AND USE THEREOF

This application is a U.S. national phase under the provisions of 35 U.S.C. § 371 of International Patent Application No. PCT/KR17/04199 filed Apr. 19, 2017, which in turn claims priority of Korean Patent Application No. 10-2016-0053018 filed Apr. 29, 2016. The disclosures of such international patent application and Korean priority patent application are hereby incorporated herein by reference in their respective entireties, for all purposes.

CROSS-REFERENCE TO RELATED APPLICATIONS

Technical Field

The present invention relates to a fusion protein comprising a CCL3 variant with improved in vivo persistency, protein stability, and pharmacological activity, more particularly, to a fusion protein comprising a CCL3 variant and an immunoglobulin Fc region, and a use thereof as a therapeutic agent for lymphopenia, cancer or infection, in which an N-terminal amino acid of a wild-type CCL3α or CCL3β is deleted and an amino acid at a specific position is substituted with a different amino acid at the same position of the wild-type CCL3α or CCL3β in the CCL3 variant.

Description of the Related Art

Chemokines are secreted by various immune cells as cytokines having chemotaxis and bind to chemokine receptors expressed in the immune cells to promote in vivo mobility of the immune cells. Among the chemokines, CC type ligand 3 (CCL3) is a chemokine that is secreted in immune cells including microphages and known to be involved in mobility of immune cells expressing a CC type receptor CCR1/CCR5, such as dendritic cells, T cells, monocytes, and neurotrophiles (Cytokine & Growth Factor Reviews (2002) 13:455-481).

CCL3, known as macrophage inflammatory protein-1α (MIP-1α), has only one subtype in mouse, but two subtypes in human (Cytokine & Growth Factor Reviews (2002) 13:455-481). Accordingly, CCL3 includes an α type (LD78α or CCL3α, hereinafter, CCL3α) having homology with that of mouse and a β type (LD78β or CCL3β, hereinafter, CCL3β) generated by mutation of genes in evolutionary process.

In the related art, it is known that CCL3 inhibits the division and differentiation of immature blood stem cells in the bone marrow of mouse and may increase the concentration of immune cells in the blood (Nat Rev Immunol. (2006) 6(2):159-64). As a result, CCL3 has been used as a therapeutic agent target for treatment of lymphopenia that is found in various anticancer agents (Exp. Hematol. (1999) 27:195-202, Cytokine & Growth Factor Reviews (2002) 13:455-481). In addition, since CCL3 has an effect of increasing the concentration of dendritic cells in the blood, it is known that the CCL3 may have potential as a novel immune cancer agent when combined with a treatment method capable of exposing a tumor-specific antigen in the blood (Clin Cancer Res. (2008) 14(4):1159-1166, European Journal of Cancer (1998) 34(7):1023-1029).

Meanwhile, since CCL3 has a very short half-life and has a tendency to be precipitated easily, CCL3 is not suitable to be used as a biotherapeutic agent without modification. Because the in vivo half-life of CCL3 intravenously injected to human body is as short as about 1.7 hours or less, if CCL3 is developed as an anti-cancer agent or a therapeutic agent for lymphopenia, the agent needs to be administered daily (European Journal of Cancer (1998) 34(7):1023-1029). Further, CCL3 is precipitated by the formation of a polymeric substance even at a concentration as low as 0.1 mg/mL.

Therefore, in order to develop CCL3 as a drug or an immune anticancer agent, a CCL3 variant (CCL3 variant) may be prepared by substituting or removing some amino acids of wild-type CCL3, and/or a fusion protein may be prepared by combining a polymer or an additional protein with CCL3. It is known that the half-life may be increased by combining a polymer or an additional protein. For example, an active protein may be bound to human albumin or polyethylene glycol (PEG). However, the residence time is increased only slightly by the binding of human albumin, and the receptor binding affinity may be reduced due to steric hindrance in the binding of PEG.

Considering this, research and development has been recently performed to increase the in vivo half-life through a fusion protein prepared by using immunoglobulin (Ig). Human Ig (hIg) includes various classes, such as IgG, IgM, IgA, IgD, and IgE, and may be further classified into various subtypes known as human IgG1 (hIgG1), human IgG2 (hIgG2), human IgG3 (hIgG3), and human IgG4 (hIgG4).

Immunoglobulin includes four polypeptide chains; two heavy chains and two light chains are linked through disulfide bonds to form a tetramer. Each chain includes a variable region and a constant region. A constant region of a heavy chain is further classified into three parts, which are CH1, CH2, and CH3, or four parts, which are CH1, CH2, CH3, and CH4, according to isotypes, and includes a hinge, CH2, CH3 and/or CH4 domains.

Under the technical background, the inventors of the present invention verified that the in vivo half-life was increased, the stability was improved, and the drug efficacy was improved in the fusion protein comprising a CCL3 variant and an immunoglobulin Fc region, in which an N-terminal amino acid of a wild-type CCL3a or CCL3β is deleted and an amino acid at a specific position is substituted with a different amino acid at the same position of the wild-type CCL3α or CCL3β in the CCL3 variant.

SUMMARY

The present invention provides a fusion protein comprising a CCL3 variant and an immunoglobulin Fc region, in which some amino acids of a wild type CCL3 are substituted and deleted in the CCL3 variant.

The present invention provides a nucleic acid encoding the fusion protein, a vector comprising the nucleic acid, and cells transformed by using the vector.

The present invention provides a method of preparing the fusion protein.

The present invention provides a pharmaceutical composition comprising the fusion protein.

The present invention provides a CCL3β variant, in which some amino acids of a wild type CCL3 are substituted and deleted in the CCL3β variant.

The present invention provides a fusion protein comprising a CCL3 variant comprising the following mutations and an immunoglobulin Fc region, in which the mutations include: (1) deletion of one or two amino acids from an N-terminal of a wild-type CCL3; and (2) substitution of aspartic acid at the position 27th amino acid from the N-terminal of the wild-type CCL3 with alanine.

The present invention provides a nucleic acid encoding the fusion protein.

The present invention provides a vector comprising the nucleic acid.

The present invention provides cells transformed with the vector.

The present invention provides a method for preparing the fusion protein.

The present invention provides a pharmaceutical composition comprising the fusion protein.

The present invention provides a CC type ligand 3β (CCL3β) variant comprising the following mutations: (1) deletion of one or two amino acids from an N-terminal of a wild-type CCL3β; and (2) substitution of aspartic acid at the position 27th amino acid from the N-terminal of the wild-type CCL3 with alanine.

The fusion protein of the present invention comprising the CCL3 variant has a desired pharmacokinetic profile because the activity reduction of the CCL3 variant is minimized, the risk of immunogenicity is low, and the in vivo half-life is increased without a stability problem, thereby improving in vivo persistency, physical properties and pharmacological efficacy of the protein. The pharmaceutical composition comprising the fusion protein comprising the CCL3 variant can be used as a therapeutic agent for lymphopenia, cancer or infection.

DETAILED DESCRIPTION OF THE PREFERRED EMBODIMENT

Figure 1:
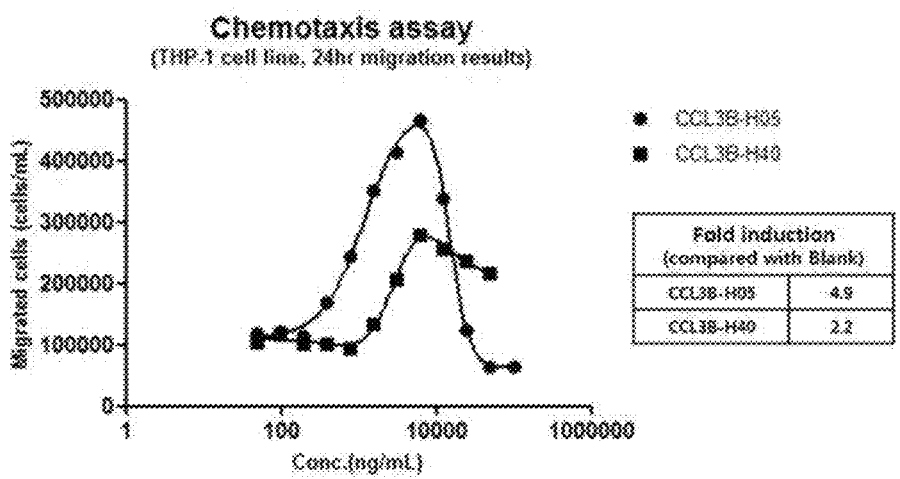
FIG. 1 is a plot showing the results of measuring in vitro chemotaxis of CCL3 variant fusion proteins CCL3B-H05 and CCL3B-H40 by using a THP-1 cell line.

Unless otherwise defined, all technical and scientific terms used in this specification have the same meaning as those commonly understood by those skilled in the art. In general, the nomenclature used in this specification is well-known and commonly used in the art.

Among various long-acting technologies for increasing the half-life of a general protein, an Fc fusion technology is most widely used because the technology may increase the in vivo half-life with less concern about side effects such as toxicity or induction of an immune response. Development of Fc fusion CCL3 and/or its variant as a drug for continuous treatment should satisfy several conditions as follows.

First, the decrease of in vitro activity by fusion needs to be small. In general, when small proteins such as chemokines are fused with Fc having a relatively large size, it is known that the activity is greatly dependent on a fusion location and a linker. Accordingly, the activity of CCL3 and/or its variant and the Fc fusion protein may vary according to the presence of fusion or a fusion location.

Second, considering that most biopharmaceuticals may cause immunogenicity in patients, the risk of immunogenicity by fusion linkers or mutations needs to be low.

Third, there should be no stability problems due to a fusion location or introduction of mutation.

Fourth, because an undesired immune response may be caused depending on an isotype of fused immunoglobulin, an alternative of the isotype of fused immunoglobulin is required.

While the inventors of the present invention made an effort to improve physiological activities and physical properties of CCL3 by considering the abovementioned conditions, it was found that artificially removing an N-terminal amino acid, introducing a mutation to a specific position of CCL3, and fusion to an immunoglobulin Fc region may increase the activity of the CCL3 to increase the vivo exposure degree and half-life and to improve the pharmacological efficacy.

Based thereon, one aspect of the present invention relates to a fusion protein comprising a CC type ligand 3 (CCL3) variant comprising the following mutations and an immunoglobulin Fc region, wherein the mutations are: (1) deletion of one or two amino acids from an N-terminal of wild-type CCL3; and (2) substitution of aspartic acid at the position 27th amino acid from the N-terminal of the wild-type CCL3 with alanine.

The CCL3 is a chemokine known to play an important role in mobility homeostasis of dendritic cells and immune cells such as T cells, monocytes, and neutrophils, and may be derived from mammals such as humans, mice, pigs, and monkeys. For example, two subtypes exist in humans. The two subtypes are an α type (hereinafter, referred to as CCL3α) having homology with that of mouse and a β (hereinafter, referred to as CCL3β) generated by mutation of genes in evolutionary process. Particularly, the wild-type CCL3 may be, for example, a human wild-type CCL3α protein comprising a sequence of SEQ ID NO: 1 or a human wild-type CCL3β protein comprising a sequence of SEQ ID NO: 3.

In one example, the CCL3 variant may include a CCL3α variant, in which the CCL3α variant is prepared by deleting alanine that is the first amino acid from an N-terminal and by substituting aspartic acid that is the 27th amino acid from the N-terminal with alanine in the human wild-type CCL3α comprising the sequence of SEQ ID NO: 1. The CCL3α variant may include for example, a sequence of SEQ ID NO: 2.

In another example, the CCL3 variant may include a CCL3β variant, in which the CCL3β variant is prepared by deleting alanine and proline (AP) that are two amino acids from an N-terminal and by substituting aspartic acid that is the 27th amino acid from the N-terminal with alanine in the human wild-type CCL3β comprising the sequence of SEQ ID NO: 3. The CCL3β variant may include, for example, a sequence of SEQ ID NO: 4.

The term "Fc region" herein means a protein without variable regions in heavy and light chains and constant region 1 in light chain (CL1) of an immunoglobulin, and the Fc region may be a hybrid Fc comprising at least one Fc region selected from the group consisting of IgG1, IgG2, IgG3, IgG4, and IgD and fragments thereof or a combination thereof.

In one example, for example the hybrid Fc may include an IgG4 region and an IgD region. Further, the hybrid Fc region may include part of the hinge sequence and CH2 of an IgD Fc, and CH2 and CH3 sequences of IgG4 Fc, for example, a sequence of SEQ ID NO: 14. The hybrid Fc may be equal to, for example, a hybrid Fc form disclosed in Korean Patent Registration No. 0897938, and introduced to this specification as a reference.

In yet another example, the Fc region may be a hybrid Fc comprising at least one Fc region selected from the group consisting of IgG1, IgG2, IgG3, and IgG4, and fragments thereof or a combination thereof.

The Fc region may include the entire Fc region constituting an immunoglobulin or may include a fragment or an Fc region variant thereof. The Fc region may also include an Fc region variant prepared by substituting some amino acids or combining different types of Fc regions. The Fc region variant may be modified for preventing cleavage at the hinge region. In addition, a part of the amino acid sequence of a hinge sequence of the Fc may be substituted in order to reduce antibody-dependent cell-mediated cytotoxicity (ADCC) or complement-dependent cytotoxicity (CDC). Further, in the hinge sequence of the Fc, a part of the amino acid sequence may be substituted in order to inhibit rearrangement of a Fab region. Furthermore, lysine (K) at the Fc region C-terminal may be removed.

Further, the Fc fragment of the present invention may be a wild-type sugar chain, an increased sugar chain compared to the wild type, a decreased sugar chain compared to the wild type, or a form in which the sugar chain is removed. The increase, decrease, or removal of the sugar chain may be performed by a general method known in this art, such as a chemical method, an enzymatic method, and a genetic engineering method using microorganisms.

The immunoglobulin Fc region may be a form in which the CCL3 variant is directly linked to an N-terminal or a C-terminal of the Fc region or linked to an N-terminal or a C-terminal of the Fc region through a linker. When the immunoglobulin Fc region is directly linked to the CCL3 variant, for example, in the present invention, the CCL3α variant of SEQ ID NO: 2 or the CCL3β variant of SEQ ID NO: 4 may be linked to an N-terminal or a C-terminal of the Fc region of SEQ ID NO: 14. The linked form of the CCL3 and the Fc may appropriately be a form in which the CCL3 is linked to an N-terminal of the Fc region.

When the immunoglobulin Fc region is linked through a linker, the linker may be linked to an N-terminal, a C-terminal, or a free radical of the Fc fragment and the may be linked to an N-terminal, a C-terminal, or a free radical of the CCL3 variant. When the linker is a peptide linker, the linkage may occur at any part. For example, the linker may be linked to a C-terminal of the Fc region of the immunoglobulin and an N-terminal of the CCL3 variant.

After a linker and the Fc are separately expressed and then linked to each other, the linker may be a crosslinker known in this art. The crosslinker may be, for example, N-hydroxysuccinimide ester such as 1,1-bis(diazoacetyl)-2-phenylethane, glutaraldehyde, and 4-azidosalicylic acid, imidoesters comprising disuccinimidyl esters such as 3,3'-dithiobis(succinimidylpropionate), and bifunctional maleimides such as bis-N-maleimido-1,8-octane, but is not limited thereto.

In addition, the linker may be a peptide. Particularly, the linker may be a peptide consisting of 10 to 30 amino acid residues. In one example, the immunoglobulin Fc region may be linked to the CCL3 variant through the linker as set forth in Formula 1 below.

$$(RNT)_nGRGG(EEKKK)_m \quad \text{(Formula 1)}$$

In Formula 1, n and m are 1 to 5, respectively. In Formula 1, n represents the repetition number of arginine-asparagine-threonine amino acids, m represents the repetition number of glutamate-glutamate-lysine-lysine-lysine amino acids, and preferably, n and m may be 1 to 3, respectively.

In one example, by considering that n and m may be 1 to 3, respectively, the linker may include any one sequence selected from the group consisting of SEQ ID NOs: 5 to 13.

One specific example of the present invention includes a structure in which the immunoglobulin Fc region is linked to the CCL3 variant through the linker comprising the sequence of RNTGRGGEEKKK (SEQ ID NO: 5). One Experimental Example of the present invention showed that the CCL3 variant fusion protein bound to the immunoglobulin Fc through the linker comprising the sequence of SEQ ID NO: 5 had excellent chemotaxis activity.

The fusion protein may be a form in which a dimer or multimer CCL3 variant is bound to the Fc region of the immunoglobulin, in which the dimer or multimer CCL3 variant is formed when one or more CCL3 variants are bound with each other. In addition, the fusion protein may be a dimer or multimer form, in which the dimer or multimer form may be two or more Fc regions are linked, wherein the immunoglobulin Fc regions have the CCL3 variant connected thereto.

Another aspect of the present invention relates to a nucleic acid encoding the fusion protein comprising the CCL3 variant.

The nucleic acid encoding the fusion protein comprising the CCL3 variant may be isolated to recombinantly produce the fusion protein comprising the CCL3 variant. The nucleic acid is isolated and inserted into a replicable vector to perform an additional cloning or expression. Based thereon, another aspect of the present invention relates to a vector comprising the nucleic acid.

The term "nucleic acid" used herein has a comprehensive meaning comprising DNA (gDNA and cDNA) and RNA molecules, and a nucleotide as a basic building block of a nucleic acid includes not only a natural nucleotide but also analogues thereof comprising a modified sugar or base site. A sequence of the nucleic acid encoding the fusion protein comprising the CCL3 variant of the present invention may be modified. The modification includes addition, deletion, or non-conservative substitution or conservative substitution of a nucleotide.

In the present invention, the term "nucleic acid" includes a nucleotide sequence having substantial identity with the respect to the sequence. The substantial identity means an amino acid sequence having at least 80% homology, more preferably at least 90% homology, and most preferably at least 95% homology, in an analysis performed by aligning the nucleic acid sequence of the present invention to correspond to an another arbitrary sequence as much as possible and then analyzing the aligned sequence by using algorithms commonly used in the art.

A DNA encoding the fusion protein comprising the CCL3 variant is easily isolated or synthesized by using a process commonly used in this art.

The term "vector" used herein refers to a means for expressing a target gene in a host cell, and includes plasmid vectors; cosmide vectors; virus vectors such as bacteriophage vectors, adenovirus vectors, retrovirus vectors, and adeno-associated virus vectors; and the like. Acceptable vector components generally include one or more of a signal sequence, a replication origin, one or more marker genes, an enhancer element, a promoter, and a transcription termination sequence, but are not limited thereto.

In the vector, the nucleic acid encoding the fusion protein comprising the CCL3 variant is operatively linked to the promoter.

The term "operatively linked" used herein means a functional binding between a nucleic acid expression regulatory sequence (for example, a promoter, a signal sequence, or an array at a binding site of a transcription regulator) and a different nucleic sequence, and the regulatory sequence regulates through the functional binding the transcription and/or translation of the different nucleic sequence.

In the case of using prokaryotic cells as a host, generally, a strong promoter (for example, a tac promoter, a lac promoter, a lacUV5 promoter, a lpp promoter, a pLX promoter, a racy promoter, an amp promoter, a recA promoter, a SP6 promoter, a trp promoter, a T7 promoter, and the like), a ribosome binding site for initiation of translation, and a transcription/translation termination sequence are generally included. In addition, for example, in the case of using eukaryotic cells as a host, promoters derived from a genome of mammalian cells (for example, a metallothionein promoter, an β-actin promoter, a human hepatoblast promoter and a human muscle creatine promoter) or promoters derived from mammalian viruses (for example, an adenovirus late-phase promoter, a vaccinia virus 7.5K promoter, a SV40 promoter, a cytomegalovirus (CMV) promoter, an HSV tk promoter, a mouse breast tumor virus (MMTV) promoter, an LTR promoter of HIV, a moloney promoter, an Epstein-Barr virus (EBV) promoter, and a promoter of rosacekoma virus (RSV)) may be used, and a polyadenylation sequence is generally included as a transcription termination sequence.

In some cases, the vector may be fused with a different sequence in order to facilitate purification of the fusion protein comprising the CCL3 variant expressed therefrom. The fused sequence includes, for example, glutathione S-transferase (Pharmacia, USA), maltose binding protein (NEB, USA), FLAG (IBI, USA), 6× His (hexahistidine; Quiagen, USA), and the like.

The vector includes as a selectable marker an antibiotic resistance gene commonly used in this art, such as genes having resistance to ampicillin, gentamycin, carbenicillin, chloramphenicol, streptomycin, kanamycin, geneticin, neomycin and tetracycline.

Another aspect of the present invention relates to cells transformed by the aforementioned vector. The cells may be prokaryotes, yeast or higher eukaryotic cells, but are not limited thereto.

*Escherichia coli, Bacillus* species strains, such as *Bacillus subtilis* and *Bacillus tulignensis*, and prokaryotic host cells, such as *Streptomyces, Pseudomonas* (for example, *Pseudomonas putida*), *Proteus mirabilis*, and *Staphylococcus* (for example, *Staphylocus carnosus*), may be used.

However, interest in animal cells is greatest, and an example of a useful host cell line may be COS-7, BHK, CHO, CHOK1, DXB-11, DG-44, CHO/−DHFR, CV1, COS-7, HEK293, BHK, TM4, VERO, HELA, MDCK, BRL 3A, W138, Hep G2, SK-Hep, MMT, TRI, MRC 5, FS4, 3T3, RIN, A549, PC12, K562, PER.C6, SP2/0, NS-0, U20S, or HT1080, but is not limited thereto.

Another aspect of the present invention relates to a method of preparing a fusion protein comprising a CCL3 variant, in which the method includes (a) culturing the cells; and (b) collecting the fusion protein in the cultured cells.

The cells may be cultured in various media. Commercially available media may be used as the culture medium without limitation. All other essential supplements known to those skilled in this art may be included at an appropriate concentration. It is obvious for the one skilled in the art to select optimal culturing conditions, for example, temperature, pH, and the like in culturing the host cells.

The recovery of the fusion protein comprising the CCL3 variant may be performed by removing impurities by, for example, centrifugation or ultrafiltration, and purifying the resulting product by using, for example, affinity chromatography and the like. Other additional purification techniques, for example, anion or cation exchange chromatography, hydrophobic interaction chromatography, hydroxylapatite chromatography, and the like may be used.

Another aspect of the present invention relates to a pharmaceutical composition comprising the fusion protein comprising the CCL3 variant.

The pharmaceutical composition may include a fusion protein comprising a CCL3 variant at an effective amount for treatment and a pharmaceutically acceptable carrier. The term "pharmaceutically acceptable carrier" refers to a material that may be added to an active component to help the formulating or stabilizing the formulation, and does not cause a significantly harmful toxic effect on a patient.

The carrier means a carrier or a diluent neither irritating a patient and nor inhibiting biological activity and characteristics. The pharmaceutical carrier acceptable for a composition formulated into a liquid solution is suitable for sterilization and biocompatible. A saline solution, sterile water, a ringer's solution, buffered saline, an albumin injection solution, a dextrose solution, a maltodextrin solution, glycerol, ethanol, and a mixture of one or more thereof may be used, and if necessary, other general additives such as antioxidants, buffers, and bacteriostats may be added. In addition, the pharmaceutical carrier may be formulated as injectable solutions, such as aqueous solutions, suspensions, emulsions, and the like, pills, capsules, granules or tablets by additionally adding diluents, dispersants, surfactants, binders and lubricants.

The pharmaceutically acceptable carrier includes a sterile aqueous solution or a dispersion and sterile powder for extemporaneously preparing a sterile injectable solution or dispersion. Use of such a medium and an agent for a pharmaceutically active substance is known in this art. The composition is preferably formulated for parenteral injection. The composition may be formulated as solutions, microemulsions, liposomes, or other ordered structures suitable for a high drug concentration. The carrier may be a solvent or a dispersive medium containing, for example, water, ethanol, polyol (for example, glycerol, propylene glycol, liquid polyethylene glycol, and the like), and an appropriate mixture thereof. In some cases, isotonic agents, for example, sugars, polyalcohols such as mannitol and sorbitol, or sodium chloride may be included in the composition. The sterile injectable solution may be prepared by mixing a required amount of active compound in a suitable solvent with one or a combination of the abovementioned components according to the need, and by performing sterile microfiltering of the resulting mixture. Generally, the dispersion agents are prepared by adding an active compound into a sterile vehicle containing a basic dispersion medium and other required components among those described above. Some methods of preparing a sterile injectable solution by using sterile powder include vacuum drying and freeze-drying to produce powder of an active component and any additional desired component from a solution thereof that has already been sterilized and filtered.

In addition, the present invention relates to a composition for treatment or prevention of CCL3-associated disorders comprising the fusion protein comprising the CCL3 variant or relates to a method for treating or preventing CCL3-associated disorders comprising administration of the fusion protein comprising the CCL3 variant into a subject requiring treatment.

The CCL3-associated disorders may include, for example, lymphopenia, various cancers, and infection. The fusion protein comprising the CCL3 variant according to the present invention may induce cancer tissue and/or cancer cell death due to activation of an immune response in association with a cancer cell death caused by irradiation. Based on this, in one example of the present invention, the fusion protein may be a composition of combining or assisting radiation treatment for treatment or prevention of.

The radiation rays may be, for example, gamma ray or X ray, and is not limited thereto, but may be irradiated at a dose of 0.1 to 50 Gy and, preferably, 0.1 to 10 Gy. The dose of the radiation rays may be adjusted within an appropriate range by considering immune deterioration and the like due to radiation side effects.

The fusion protein comprising the CCL3 variant may be administered through any routes. For example, the fusion protein comprising the CCL3 variant may be provided to animals directly (for example, by injecting, implanting, or locally administering the fusion protein into a tissue part, locally) or systematically (for example, parenterally or orally) by any appropriate means.

In the case of parenteral administration, such as intravenous, subcutaneous, ophthalmic, intraperitoneal, intramuscular, oral, rectal, intraorbital, intracerebral, intracranial, intraspinal, intraventricular, intrathecal, intracistenal, intracapsular, intranasal, or aerosol administration, for example, a part of an aqueous or physiologically compatible body-fluid suspension or solution may be included. Accordingly, since the carrier or the vehicle is physiologically acceptable, the carrier or the vehicle may be added to the fusion protein to be transferred to the patient. Therefore, as the carrier such as a body fluid for formulation, generally, a saline solution may be included.

A dose frequency varies according to pharmacokinetic parameters of the fusion protein comprising the CCL3 variant in the formulation used. Typically, a clinical doctor may administer the fusion protein until reaching a dose achieving a desired effect. Accordingly, the fusion protein may be administered as a single dose, as two or more doses (with or without comprising the same amount of target fusion protein) with a time interval, or as continuous injection through a graft device or a catheter. Additional refinement of the appropriate dose is routinely achieved by those skilled in this art and corresponds to a work field routinely performed by those skilled in this art.

A unit dose is 0.01 μg/kg to 100 mg/kg, particularly, 1 μg/weight kg to 30 mg/weight kg in humans. The dose is an optimal dose, but may be depending on the diseases to be treated and the existence of side effects, and the optimal dose may be determined by performing experiments commonly carried out. The administration of the fusion protein may be performed by periodic bolus injections or continuous intravenous, subcutaneous, or intraperitoneal administration from an external reservoir (for example, an intravenous bag) or an internal reservoir (for example, a bioerodable implant).

The administration frequency varies according severity of a disease. The administration frequency may be in a range of three times per week to once per week or once every two weeks.

In some cases, the fusion protein comprising the CCL3 variant may be administered to a target receptor with other biologically active molecules. However, an optimal combination, a dosage form, and an amount of the fusion protein and other molecules may be determined through a common experiment well-known in this art.

The term "effective amount for treatment" used herein refers to a sufficient amount to treat a disease at a reasonable benefit/risk ratio applicable to medical treatment and means an amount of the fusion protein comprising the CCL3 variant according to the present invention. An accurate amount varies according to many factors that include components and physical characteristics of the therapeutic composition, an intended patient population, individual patient considerations, and the like, but are not limited thereto, and may be easily determined by those skilled in this art. When completely considering these factors, it is important to administer a minimum amount sufficient to achieve a maximum effect without side effects and the dose may be easily determined by experts in this art.

The dose of the pharmaceutical composition of the present invention is not particularly limited, but is changed by various factors comprising the health condition and weight of a patient, the severity of the disease, the kind of the drug, the administration route and the administration time. The composition may be administered into mammals comprising rats, mice, livestock, humans, and the like once or multiple times daily through a typically acceptable route, for example, orally, rectally, intravenously, subcutaneously, intrauterinely, or intracerebrovascularly.

Another aspect of the present invention relates to a CC type ligand 3β (CCL3β) variant comprising the following mutations: (1) deletion of one or two amino acids from an N-terminal of a wild-type CCL3β; and (2) substitution of aspartic acid at the position 27th amino acid from the N-terminal of the wild-type CCL3 with alanine.

In one example of the present invention, the CCL3β variant may include, for example, a sequence of as set forth in SEQ ID NO: 4. The CCL3β variant of the present invention equally includes the above mentioned structures and the description for duplicated configurations is equally applied even to the invention of the CCL3β variant.

Unless otherwise defined in the technical and scientific terms used in the present invention, the present invention has a meaning which is generally understood to those skilled in the art. Further, the repeated description for the same technical configuration and operation as those in the related art will be omitted.

EXAMPLES

Hereinafter, the present invention will be described in more detail through Examples. However, it is apparent to those skilled in the art that the present invention is not limited to the following Examples, and various modifications and changes may be made within the idea and scope of the present invention.

Preparation Example 1. Preparation and Purification of Fusion Protein Comprising CCL3 Variant A mutation study on CCL3 was conducted to improve physical properties and activity profiles of the CCL3 in a CCL3-

Particularly, in order to determine whether the difference of activity between an α type (hereinafter, referred to as CCL3α) and a β type (hereinafter, referred to as CCL3β) of the CCL3 protein is maintained even after Fc fusion, various variants were constructed. In addition, in order to inhibit the precipitation of the CCL3 in the Fc fusion protein type, a variant in which the 27th aspartic acid was substituted with alanine was designed.

Locations, sequence information, objects, and expected effects of each mutation introduced into the CCL3 were summarized in Table 1 below.

TABLE 1

| Designation of Sequences | Position | Original Sequence | Mutation Sequence | Object | Expected Effect |
|---|---|---|---|---|---|
| D27A | 27 | D | A | Point mutation | Improvement of physical properties through inhibition of precipitation |
| Δ1 | 1 | A | — | Amino acid deletion | Improvement of physical properties |
| Δ1-2 | 1-2 | AS or AP | — | Amino acid deletion | Improvement of pharmacological effect |
| CCL3α | 2, 39, 47 | S, G, S | — | — | — |
| CCL3β | 2, 39, 47 | P, S, G | — | — | — |

Amino acids were encoded in an expression vector to express three constituent elements in the order of the CCL3 variant, a linker, and a fusion carrier from an N-terminal to a C-terminal. Table 2 below summarizes symbols of the CCL3 variant fusion proteins, mutation sequences introduced into the CCL3, fusion carrier sequences, and linker sequences.

TABLE 2

| Protein Code | CCL3 mutation sequence | Fusion carrier sequence | Linker sequence |
|---|---|---|---|
| CCL3 | D27A, Δ1, CCL3α (SEQ ID No: 2) | N/A | N/A |
| CCL3A-H05 (SEQ ID No: 15) | D27A, Δ1, CCL3α (SEQ ID No: 2) | hyFc (SEQ ID No: 14) | H05 (SEQ ID No: 5) |
| CCL3B-H05 (SEQ ID No: 16) | D27A, Δ1-2, CCL3β (SEQ ID No: 4) | hyFc (SEQ ID No: 14) | H05 (SEQ ID No: 5) |
| CCL3B-H40 (SEQ ID No: 17) | D27A, Δ1-2, CCL3β (SEQ ID No: 4) | hyFc (SEQ ID No: 14) | N/A |

In order to produce the CCL3 variant fusion protein, a nucleotide sequence encoded based on an amino acid sequence of the CCL3 variant fusion protein was synthesized by Bioneer Co., Ltd. (Korea). NheI and NotI restriction enzyme sequences were added to a 5'-terminus and a 3'-terminus of the nucleotide sequence encoding each CCL3 variant fusion protein, respectively, and a start codon for protein translation and an induction sequence for secreting the expressed protein extracellularly were inserted after the restriction enzyme sequence of the 5'-terminus. A termination codon was inserted after the nucleotide sequence encoding each CCL3 variant fusion protein. A nucleotide sequence encoding each CCL3 variant fusion protein was cloned in a pTrans-empty expression vector by using the two restriction enzyme sequences NheI and NotI. The pTrans-empty expression vector obtained from CEVEC Corporation in Germany was a simple structural expression vector having a CMV promoter, a pUC-derived replication origin, an SV40-derived replication origin, and an ampicillin resistance gene.

Preparation Example 1-2. Preparation of Plasmid DNA for Expression of CCL3 Variant Fusion Protein A large amount of plasmid DNAs to be used for expression was obtained by transforming each expression vector prepared in Preparation Example 1-1 to *E. coli*. Each expression vector was transduced through heat shock into *E. coli* with a weakened cell wall, and the resulting transduced *E. coli* was smeared on an LB plate to obtain colonies. The obtained colonies were inoculated into an LB medium and cultured at 37° C. for 16 hours, and 100 mL of *E. coli* having respective expression vectors in the cells was obtained, respectively. After removing a culture medium through centrifugation, solutions P1, P2, and P3 (QIAGEN, Cat #12963) were added to the *E. coli* to obtain a DNA turbid solution by breaking the cell wall and isolating the protein and the DNA. The plasmid DNAs were purified from the obtained DNA turbid solution by using a Qiagen DNA purification column. The eluted plasmid DNAs were confirmed by agarose gel electrophoresis and used for expression after measuring a concentration and purity by using a nanodrop device (Thermo scientific, Nanodrop Lite).

Preparation Example 1-3. Expression of Fusion Protein in CAP-T Cells

A human cell line was transformed with each plasmid DNA isolated in Preparation Example 1-2. Each plasmid DNA was transduced into CAP-T cells (CEVEC) while being cultured in a PEM medium (Life technologies) by using a PEI solution (Polyplus, Cat #101-10N) A mixed solution of the DNA and the PEI solution was mixed with suspended cells by using a Freestyle 293 expression medium of Invitrogen Corporation, cultured at 37° C. for 5 hours, and then added with a PEM medium. After culture at 37° C. for 5 to 7 days, the cells were removed by centrifugation to obtain a supernatant comprising the CCL3 variant fusion protein.

Preparation Example 1-4. Purification of CCL3 Variant Fusion Protein

Impurities were removed from the culture supernatant comprising the CCL3 variant fusion protein by using a 0.2 μm filter and then a protein A affinity chromatography column (GE Healthcare) was equilibrated with a 1×PBS (pH 7.4) buffer. The column was washed with the 1×PBS (pH 7.4) buffer and then the protein was eluted with a 100 mM glycine (pH 3.0) buffer. The CCL3A-H05 fusion protein (SEQ ID NO: 15) obtained through the affinity chromatography was purified by using a hydroxyapatite type I column (Ceramic Hydroxyapatite type I, 40 μM, Bio-rad), and the CCL3B-H05 fusion protein (SEQ ID NO: 16) and the CCL3B-H40 fusion protein (SEQ ID NO: 17) were purified by using a hydroxyapatite type I column (Ceramic Hydroxyapatite type II, 40 μM, Bio-rad). The hydroxyapatite column was equilibrated with a 20 mM sodium phosphate (pH 7.2) buffer and then the eluted CCL3 variant fusion protein was loaded on the affinity chromatography. Particularly, the column was washed with the 20 mM sodium phosphate (pH 7.2) buffer, the 20 mM sodium phosphate (pH 7.2) buffer flowed at a concentration gradient, and then eluted fractions were analyzed. Each fraction was analyzed by using a size exclusion chromatography (SEC-HPLC) assay, and portions comprising the high-purity CCL3 variant fusion protein were collected and then dialyzed overnight at 4° C. with the final buffer 1×PBS. A protein crude solution obtained by the dialysis was concentrated at 3,000 rpm at 4° C. by using a 30,000 molecular-weight cutoff centrifugal filter. The concentration of the CCL3 variant fusion protein was measured by a BCA quantitative analysis.

Experimental Example 1. Result of Measuring In Vitro Activity of Fusion Protein

Experimental Example 1-1. Result of Measuring Activity According to Linker Sequence The in vitro activity of CCL3 variant fusion proteins CCL3B-H05 (SEQ ID NO: 16) and CCL3B-H40 (SEQ ID NO: 17) prepared in the above Preparation Examples was measured.

In particular, in order to evaluate the in vitro activity of the fusion proteins, a THP-1 cell line ATCC in which receptors CCR1 and CCR5 of the CCL3s were expressed was used. In order to evaluate the activity, a concentrate comprising the fusion proteins obtained in the Preparation Examples were twice-series diluted and prepared at a concentration of 100 µg/mL by using an analysis medium (0.01% BSA in RPMI 1640 Medium), and the THP-1 cell line was transferred to the analysis medium and then diluted at 5,000,000 cells/mL. A polycarbonate transwell system (Costar, Cat #3422) was used to treat the bottom wells with 600 µL of the diluted fusion protein and the top inserts with 100 µL of the diluted THP-1 cell line, and then the system was kept in a 5% $CO_2$ incubator at 37° C. for reaction. After 24 hours, the inserts were removed, and the cells were stained with a trypan blue solution (Sigma, Cat #T8154-100ML) and the number of transferred cells was measured by using a cell counter (Invitrogen, Luna cell counter). The activity was compared by calculating an increase in the maximum number of migrated cells in comparison with the number of cells in a control group treated with the analysis medium, and the results are shown in FIG. 1.

As shown in FIG. 1, the result of the measured activity depending on the linkers showed that the chemotaxis of the fusion protein CCL3B-H05 was higher than that of CCL3B-H40.

Experimental Example 1-2. Result of Measuring Activity According to CCL3 Variant The in vitro activity of the fusion protein CCL3A-H05 of the sequence of SEQ ID NO: 15 and the fusion protein CCL3B-H05 of the sequence of SEQ ID NO: 16 prepared in the above Preparation Examples was measured.

Figure 2:
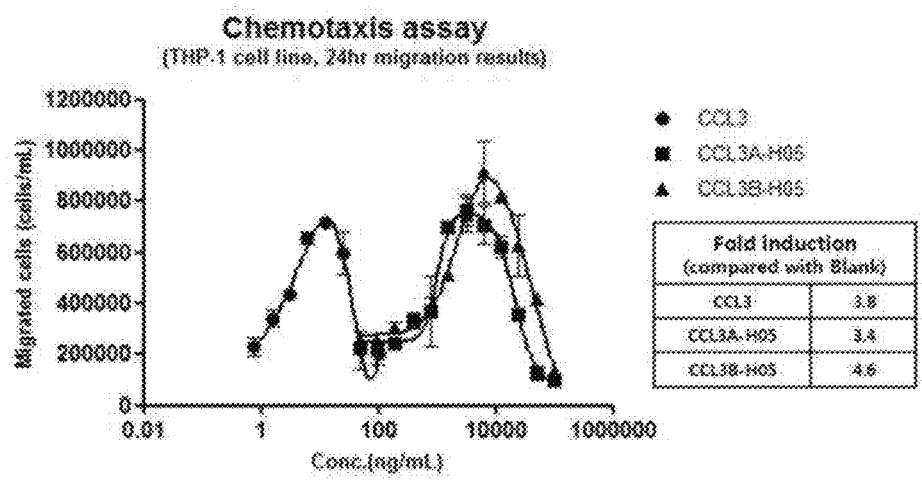
FIG. 2 is a plot showing the results of measuring in vitro chemotaxis of CCL3 and CCL3 variant fusion proteins CCL3A-H05 and CCL3B-H05 by using a THP-1 cell line.

Particularly, in a concentrate comprising the fusion proteins obtained in Preparation Examples, chemotaxis of the fusion proteins were measured by the same method as Experimental Example 1-1, and the results are shown in FIG. 2.

Experimental Example 1-3. Result of Measuring Activity According to CCL3 Variant The in vitro activity of the fusion protein CCL3A-H05 of the sequence of SEQ ID NO: 15 and the fusion protein CCL3B-H05 of the sequence of SEQ ID NO: 16 prepared in the above Preparation Example was measured.

Particularly, in order to evaluate reactivity to the receptor CCR1 of the fusion protein, a Tango™ CCR1-bla U2OS DA cell line in which the receptor CCR1 of the fusion protein was expressed and an analysis kit (Invitrogen, Cat #K1793) were used. For evaluating the activity, the Tango™ CCR1-bla U2OS DA cell line was diluted with a basic medium (FreeStyle™ Expression Medium) to the concentration of 312,500 cells/mL, 32 µL of the diluted cell line was added to a 384-well plate (Corning, Cat #3712), and then stored in a 5% $CO_2$ incubator for 16 to 24 hours. The concentrate comprising the fusion proteins obtained in the Preparation Example was diluted to the concentrations of 10 µM for CCL3 and 25 µM for CCL3A-H05, which were 5 times higher than the treatment concentration by using the analysis medium (0.5% DMSO in FreeStyle™ Expression Medium). The prepared fusion proteins were added to wells comprising the cells by 8 µL to each well to treat the cells with the twice-series diluted fusion proteins at actual concentrations of 2 µM for CCL3 and 5 µM for CCL3A-H05 and CCL3B-H05, and the treated cells were kept in a 5% $CO_2$ incubator at 37° C. for 5 hours for reaction. A 6× substrate mixed solution (6 µL of 1 mM LiveBLAzer™-FRET B/G (CCF4-AM) Substrate+60 µL of solution B+904 µL of Solution C+30 µL of Solution D) was prepared by using the solution contained in the analysis kit, and then 8 µL of the resulting mixed solution was added to each of the wells in the 384-well plate treated with the fusion protein, and then the cells were kept at room temperature for 2 hours for reaction. A ratio (Blue/Green Emission ratio) of the reacted cells and the unreacted cells was measured and calculated by a microplate reader (Molecular devices, Flexstation 3), and the results are shown in FIG. 3.

Figure 3:
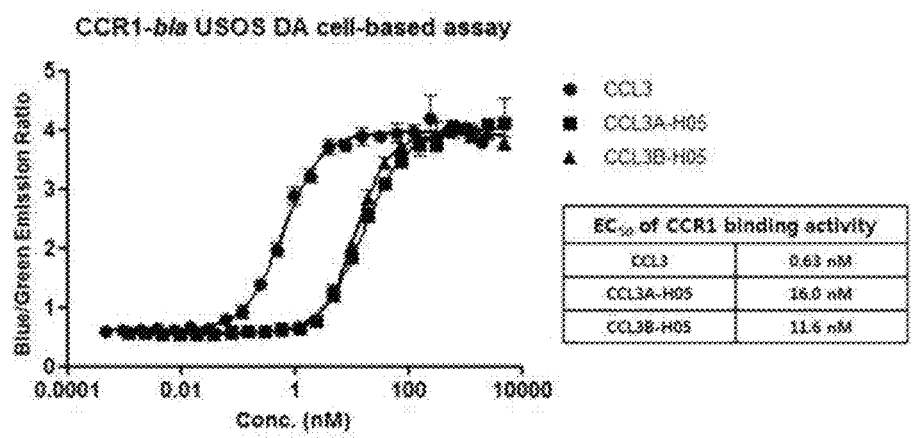
FIG. 3 shows a result of measuring in vitro activity of CCL3 and CCL3 variant fusion proteins CCL3A-H05 and CCL3B-H05 by using a cell line in which CCR1 is expressed, in order to evaluate reactivity of CCR1 receptors of the fusion proteins.

As shown in FIG. 3, the reactivity of the CCR1 receptor was at levels of 0.63 nM for CCL3, 16.0 nM for CCL3A-H05, and 11.6 nM for CCL3B-H05.

Experimental Example 2. Evaluation of Physical Properties of Fusion Protein

Experimental Example 2-1. Experimental Method for Evaluating Stability

In order to determine an amount of protein aggregates in an initial state of the sample, the content (% HMW) of high molecular weight aggregates was measured by using a size exclusion chromatography (SEC-HPLC) method.

Specifically, the SEC-HPLC method was performed by using a Tosoh model TSK-GEL G3000SW$_{XL}$ column. A Buffer 1×PBS was flowed into the column at a flow rate of 1 mL/min to equilibrate the column. The CCL3B-H05 protein stock solution obtained in Preparation Example 1-4 was concentrated at 3000 rpm and 4° C. to a target concentration of 9.5 mg/mL or higher by using a 30,000 molecular weight cutoff centrifugal filter. The concentration of each sample was measured by BCA quantitative analysis, and then the sample was stored at −70° C. for 5 weeks for stability evaluation. In order to measure the high molecular weight aggregate ratio (% HMW), 9.57 mg/mL of the sample was diluted with 1×PBS to the concentration of 1 mg/mL, and the high molecular weight aggregate ratio was analyzed by injecting 100 µL of the diluted sample into an SEC-HPLC column.

As shown in Table 3, the results verified that % HMW of the CCL3B-H05 was low and the physical property of the CCL3 variant fusion protein was improved without being disturbed by Fc fusion, as a D27A mutant was introduced and thus the % HMW was significantly decreased.

TABLE 3

Stability (% HMW) of CCL3B-H05 at concentration of 9.5 mg/mL

| CCL3B-H05 at 0 day | CCL3B-H05 at 5 weeks (37° C.) |
|---|---|
| 1.2% | 1.0% |

As Table 3 shows, an amount of % HMW at an initial stage (0 day of storage) of storage was not increased but maintained after 5 weeks of storage at −70° C. It is shown that the stability of the fusion protein CCL3B-H05 is maintained regardless of the mutation.

Experimental Example 3. Pharmacokinetic Measurement of Fusion Protein

Test Example 3-1. Experimental Method for Pharmacokinetic Measurement

Seven-week-old male C57BL/6 mice purchased from Orient BIO Corporation in Korea were group-separated (n=3 per blood collection time) to have similar average body weights on a day before the drug treatment, and then 3 mg/kg and 10 mg/kg of the samples were intravenously administered once, respectively, and the blood samples were collected at 0.083, 0.5, 1, 4, 8, 12, 24, 48, 72, 96 and 144 hours. In order to measure the blood concentration of the fusion protein, a Human CCL3/MIP-1a Quantikine ELISA kit (R&D systems, Cat #SMA00) having immunoreactivity to the CCL3 was used in this experiment. Pharmacokinetic parameters were calculated by measuring the blood concentration of CCL3B-H05 in blood sample up to 144 hours after each fusion protein was intravenously injected into mice.

Experimental Example 3-2. Result of Measuring Pharmacokinetic Activity

Figure 4:
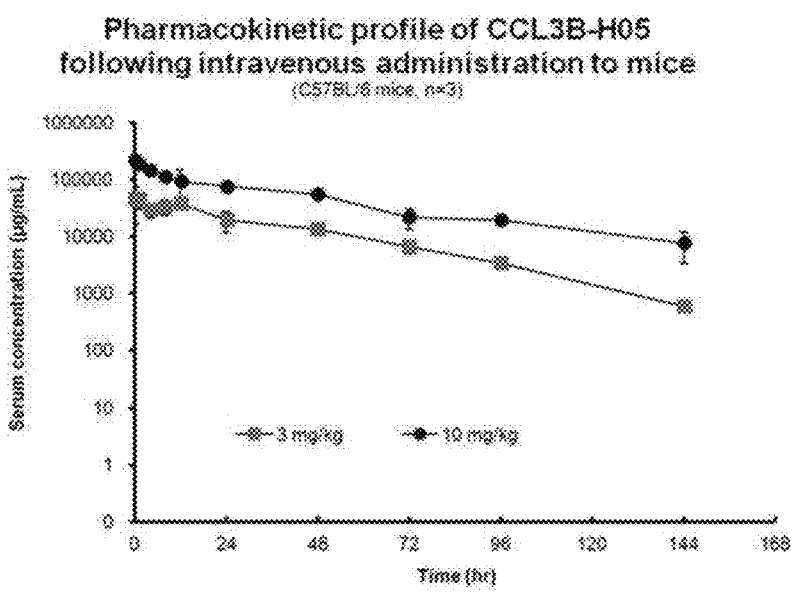
FIG. 4 shows a result of calculating a pharmacokinetic parameter by measuring a blood concentration of CCL3B-H05 in a blood sample until 144 hours after intravenously injecting the CCL3 variant fusion protein CCL3B-H05 to mice at doses of 3 mg/kg and 10 mg/kg, respectively.

The pharmacokinetic parameters were calculated based on the blood concentration plot (FIG. 4) over time following the intravenous administration of the fusion protein to the mice, and the calculation results are shown in Table 4 below.

TABLE 4

| Parameters | 3 mg/kg | 10 mg/kg |
|---|---|---|
| AUC$_{last}$ (μg · hr/mL) | 1639403.7 | 6549244.7 |
| Half-life (Hour) | 20.4 | 45.6 |
| Total clearance (mL/hr/kg) | 0.0018 | 0.0018 |
| Vd$_{ss}$ (mL/kg) | 0.0635 | 0.0636 |
| C$_0$ (μg/mL) | 46741.6 | 227907.4 |

A pharmacokinetic profile of the fusion protein was compared and evaluated based on area under the curve (AUC), which indicated the degree of exposure to the drug.

As shown in Table 4, when CCL3B-H05 was intravenously administered to the mice at doses of 3 and 10 mg/kg, body exposure was generally increased in proportion to the dose, and clearance (CL) and distribution volume (Vd$_{ss}$) were not significantly dependent on the dose, and thus a linear PK was found in the dose range of 3 to 10 mg/kg. The results also showed that a half-life ($t_{1/2}$) of the CCL3B-H05 was 20.4 hours and 45.6 hours for each dose of 3 and 10 mg/kg and increased approximately 12 to 27 times larger than the half-life (within 1.7 hours during intravenous administration in the human) of the CCL3. Considering that the half-life in mice is generally shorter than the half-life in humans, the increase of the half-life of CCL3B-H05 in comparison with the half-life of CCL3 is expected to be larger in mice.

Experimental Example 4. Evaluation of Activity of Fusion Protein in Mice

Figure 6:
FIG. 6 shows a drug treatment schedule in Experimental Example 4.

Experimental Example 4-1. Experimental Method of Anticancer Efficacy in BNL 1ME A.7R.1 Liver Cancer Allograft Mice Seven-week-old male Balb/c mice purchased from Orient BIO Corporation in Korea were acclimated for one week, and then 1×10$^7$ cells of BNL 1ME A.7R.1 (ATCC) which was a mouse liver cancer cell line were injected into the right hindlimb. At the time when a tumor volume was 120 to 150 mm$^3$, groups were separated so that the tumor volume became similar. The experimental groups and the drug treatment schedule for each group are shown in Tables 5 and FIG. 6, respectively. From the first day of drug treatment, the tumor volume was measured by using a caliper every 3 to 4 days to observe the tumor growth inhibitory efficacy of the drug (tumor volume=long axis×(short axis)$^2$/2).

TABLE 5

| Group | Route of administration | Dosage | Regimen | Number |
|---|---|---|---|---|
| G1 | Control | — | — | 8 |
| G2 | IR | — | 6.5 Gy | — | 8 |
| G3 | IR + CCL3A-H05 | IV | 6.5 Gy/10 mg/kg | q2dx3 | 8 |
| G4 | IR + CCL3B-H05 | IV | 6.5 Gy/10 mg/kg | q2dx3 | 8 |

Figure 5:
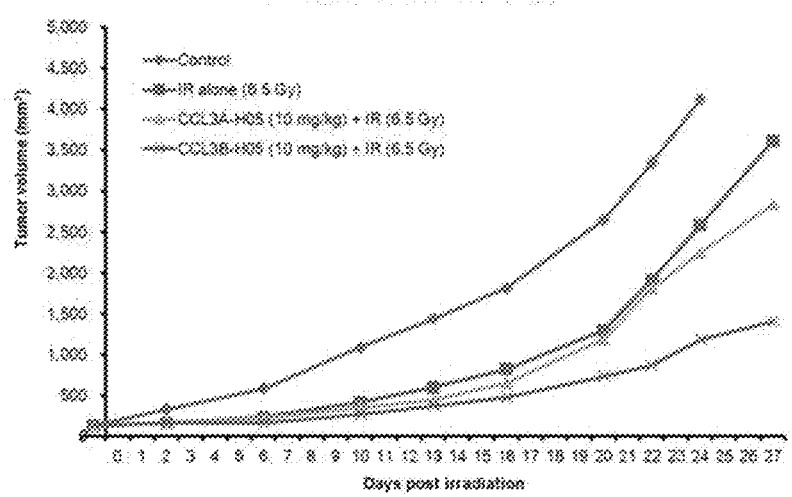
FIG. 5 shows the effect of the tumor growth inhibition of the CCL3 variant fusion protein CCL3B-H05 on a mouse liver cancer.

Experimental Example 4-2. Result of Evaluating Anticancer Efficacy in BNL 1ME A.7R.1 Liver Cancer Allograft Mice The tumor growth inhibitory efficacy of the fusion protein CCL3A-H05 comprising the sequence of SEQ ID NO: 15 and the fusion protein CCL3B-H05 comprising the sequence of SEQ ID NO: 16 prepared in the above Preparation Examples was verified on BNL 1ME A.7R.1 mouse liver cancer. As shown in FIG. 5, the tumor growth inhibitory efficacy was approximately 25% in a group treated with CCL3A-H05 10 mg/kg and approximately 72% in a group treated with CCL3B-H05 10 mg/kg as compared to a group treated with 6.5 Gy of only single irradiation after one month from the irradiation.

Although the specific part of the present invention has been described in detail, it is obvious to those skilled in the art that such a specific description is just a preferred embodiment and the scope of the present invention is not limited. Thus, the substantial scope of the present invention will be defined by the appended claims and equivalents thereof.

What is claimed is:

1. A fusion protein comprising a variant of CC type ligand 3β (CCL3β) and an immunoglobulin Fc region:
   wherein the CCL3β variant comprises the sequence of SEQ ID NO: 4
   wherein the CCL3β variant is linked to an immunoglobulin Fc region through a linker comprising the sequence of SEQ ID NO: 5, and
   wherein the immunoglobulin Fc region comprises the sequence of SEQ ID NO: 14.

2. A nucleic acid encoding the fusion protein according to claim 1.

3. A vector comprising the nucleic acid according to claim 2.

4. A cell transformed by the vector according to claim 3.

5. A method of preparing a fusion protein according to claim 1, said method comprising:
   (a) culturing a cell transformed by a vector comprising a nucleic acid encoding said fusion protein; and
   (b) collecting the fusion protein from the cultured cell.

6. A method for treating a cancer comprising administering a pharmaceutical composition comprising the fusion protein according to claim 1.

7. The method according to claim 6, wherein the composition is administered in combination with radiation treatment.

8. The method according to claim 6, wherein the composition is administered to assist radiation treatment.

* * * * *

UNITED STATES PATENT AND TRADEMARK OFFICE
CERTIFICATE OF CORRECTION

PATENT NO. : 11,046,742 B2
APPLICATION NO. : 16/097572
DATED : June 29, 2021
INVENTOR(S) : Su Youn Nam Page 1 of 1

It is certified that error appears in the above-identified patent and that said Letters Patent is hereby corrected as shown below:

In the Specification

Column 7, Line 19, "pLX" should be -- pL$\lambda$ --.

Column 7, Line 20, "racy" should be -- rac5 --.

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*